United States Patent
Lazarus et al.

[11] Patent Number: 5,407,019
[45] Date of Patent: Apr. 18, 1995

[54] APPARATUS AND METHOD FOR ENVIRONMENTAL SURVEYING FOR CONTAMINANTS IN ALLUVIAL MATERIALS AND BEDROCK FORMATIONS

[75] Inventors: Jay L. Lazarus, Santa Fe County; Van G. Baehr; Steve Slade, both of Santa Fe, all of N. Mex.

[73] Assignee: Venture Probe, Inc., Santa Fe, N. Mex.

[21] Appl. No.: 126,907

[22] Filed: Sep. 24, 1993

[51] Int. Cl.⁶ ............................................. E21B 3/12
[52] U.S. Cl. ..................................... 175/50; 175/71
[58] Field of Search ............... 175/71, 94, 95, 107, 175/20, 50, 415, 417

[56] References Cited

U.S. PATENT DOCUMENTS

| | | |
|---|---|---|
| 1,668,327 | 5/1928 | Manning . |
| 3,084,553 | 4/1963 | Cullinan et al. . |
| 3,774,701 | 11/1973 | Weaver . |
| 3,899,033 | 8/1975 | Van Huisen ............... 175/103 X |
| 4,120,368 | 10/1978 | Johansson ................ 175/94 X |
| 4,310,057 | 1/1982 | Brame . |
| 4,332,301 | 6/1982 | Jonell . |
| 4,565,086 | 1/1986 | Orr, Jr. . |
| 4,635,735 | 1/1987 | Crownover . |
| 4,786,804 | 11/1988 | Ilmasti . |
| 4,807,707 | 2/1989 | Handley et al. . |
| 4,834,194 | 5/1989 | Manchak, Jr. . |
| 4,844,807 | 7/1989 | Manchak, Jr. . |
| 4,887,464 | 12/1989 | Tannenbaum et al. . |
| 5,010,776 | 4/1991 | Lucero et al. . |
| 5,035,149 | 7/1991 | Wierenga . |

OTHER PUBLICATIONS

"Monitoring Well Drilling, Soil Sampling, Rock Coring, and Borehole Logging" by H. E. Hank Davis et al, pp. 195-237.

*Primary Examiner*—William P. Neuder
*Attorney, Agent, or Firm*—Sue Z. Shaper; Butler & Binion

[57] ABSTRACT

Apparatus and method for environmental surveying for contaminants in alluvial materials and bedrock formations including using a portable pneumatic rotary percussion drilling machine with an air compressor that powers the drilling and provides an air circulation fluid, the machine also utilizing a perforated rock drill bit and hollow stem drill rod; a vacuum pump is connectable with the hollow stem drill rod for sampling.

16 Claims, 2 Drawing Sheets ns in alluvial materials and bedrock formations. More particularly, the invention relates to a system for the use of drilling apparatus and associated equipment for effective and efficient sampling and analyzing soil vapors, collecting soil and water samples, completing ground water monitoring wells, if desired, and installing and testing air sparging and vacuum extraction remediation apparatus through both soil and bedrock.

BACKGROUND OF THE INVENTION

The invention comprises an effective, efficient, and economical system for in-situ sampling, testing, detection and/or for preparation for remediation of soil, bedrock, and ground water contamination. The system provides for the collection of soil vapor, for the collection of soil and bedrock samples from discrete intervals and for the collection of ground water samples. The system facilitates the construction of temporary or permanent ground water monitoring wells for collecting ground water samples and in-situ air permeability testing. The system affords multiple site characterization techniques for investigating and remediating contaminated soils and ground water.

At locations where soil, bedrock, and/or ground water contamination occurs, it is often desirable to collect soil vapor data from the site to determine the extent of vapor phase contamination. A monitoring system to sample soil vapor would have enhanced effectiveness, efficiency, and economy if the same apparatus could be used to collect soil samples, ground water samples and to complete ground water monitoring wells, as desired or required. It would also be desirable to have the above apparatus capable of installing and testing remediation equipment. The system would have even further general application if the drilling mechanism were capable of boring through bedrock and consolidated formations as well as through alluvial materials and unconsolidated formations. Prior to this invention, drilling systems have not been offered to provide this effective and efficient combination of field data collection and well completion techniques through soil and bedrock.

Prior and present art soil vapor surveying techniques use hand drilling and hydraulic drilling. The industry has stayed away from pneumatic drilling because of a general belief that pneumatic drilling would distort the soil vapor data. The present inventors, faced with the daunting task of environmental surveying through bedrock, experimented nonetheless with pneumatic drilling, notwithstanding the negative reception it receives in the art. The inventors learned that, unexpectedly, an air balance is apparently achieved downhole. Air pressure and venturi effects may cancel each other out at the probe tip. Pneumatic drilling can be used for environmental sampling and it does not impermissibly dilute or destroy the soil vapors sampled or the significance of the vapor analysis data.

In contrast to prior art soil vapor sampling machines and techniques, the present invention, through the use of pneumatic drilling equipment, is not only able to sample through bedrock but also is able to efficiently and effectively provide a technique capable of water sampling as well as soil sampling and capable of the installation of ground water monitoring wells in both alluvial materials and bedrock formations. The subject invention provides the synergistic advantage of performing multiple field investigative tasks both in alluvial and bedrock subsurface environments. By performing soil vapor surveys, collecting soil and/or ground water samples for laboratory analysis, and installing ground water monitoring wells and remediation equipment in both bedrock and alluvial materials, the system qualifies uniquely to offer a range of field services not currently found in the trade.

Some specific advantages of the system's drilling apparatus and technique are that it uses conventional rock bits which allow a rapid drilling rate in both alluvial and bedrock environments. Consequently, site characterization and the remediation of contaminated sites can be achieved at a rapid pace, allowing the system to provide more information to land owners for a lesser cost than the alternative of using a combination of prior systems. Furthermore, the drill cuttings (contaminated wastes) produced by the drilling apparatus and technique are of substantially less volume than that produced by many other drilling techniques, thereby reducing contaminated soil disposal costs. Because of the drilling procedure utilized, the apparatus provides a cleaner borehole wall than that offered by other drilling techniques. A cleaner borehole wall allows any remediation system installed to become effective more quickly. The apparatus and system of the present invention is further unique in the trade in that in addition to investigative techniques, it can be utilized to both install and test air sparging/vacuum extraction remediation systems. Once the remediation equipment is installed (sparge or vacuum point), the machine may be used to inject air into the sparge pipes and measure air pressure responses in the borehole located at varying distances from the air injection point. This data can then be used to determine the effective air permeability of soils/bedrock for the efficient design of remediation systems which use air sparging/vacuum extraction independently or together. As cost control is becoming an increasingly important issue for environmental investigation and remediation, an apparatus and system that performs more efficiently and effectively both investigative and remediation tasks through a variety of subsurface environments is of enhanced value.

SUMMARY OF THE INVENTION

The invention comprises an apparatus for environmental surveying for contaminants in alluvial materials and bedrock formations. The apparatus includes a portable pneumatic rotary percussion drilling machine having an air compressor for powering the drilling and for providing an air circulation fluid. The machine utilizes a perforated rock drill bit and hollow stem drill rod. The apparatus also includes a vacuum pump and means for connecting the vacuum pump with the hollow stem drill rod.

The apparatus may include means for collecting cuttings from the air circulation fluid and means for collecting fluids pumped up the hollow stem rod. The apparatus may include means for testing collected fluids, as well as a soil and bedrock sampling tool and means for connecting the sampling tool to the drill rod.

The apparatus may further include air sparging and vacuum extraction piping for installation into a drill borehole and means for connecting the air compressor of the drilling machine to the installed piping. When the air compressor is connected to the piping, meters will be employed for monitoring air pressure and air flow rate in the piping downhole. In preferred embodiments, means for measuring soil vapor concentration is connected to the exhaust of the vacuum pump and the drill rod is hexagonal.

The invention also comprises a method for environmental sampling and monitoring alluvial soil and bedrock. The method includes pneumatically drilling a borehole with a portable rotary percussion drilling machine using a perforated rock drill bit and hollow stem drill rod. Air is circulated through the stem and borehole as a circulation fluid, thereby displacing drill cuttings. A vacuum pump is connected to the hollow stem drill rod and underground fluid is lifted by means of the pump through the bit in the rod. The extracted fluids may be collected and analyzed. The method may include placing the drill bit with a soil sampling tool and pneumatically driving the tool to collect soil samples at a target depth. The method may further include withdrawing the drilling rod and machine from the borehole and installing air sparging and vacuum extraction piping. The drilling machine compressor may then be connected to the piping and air injected into the piping. Air pressure and air flow rate may be monitored under such circumstance in order to understand the characteristics of the formation around the borehole.

DETAILED DESCRIPTION OF THE PREFERRED EMBODIMENTS

Figure 2:
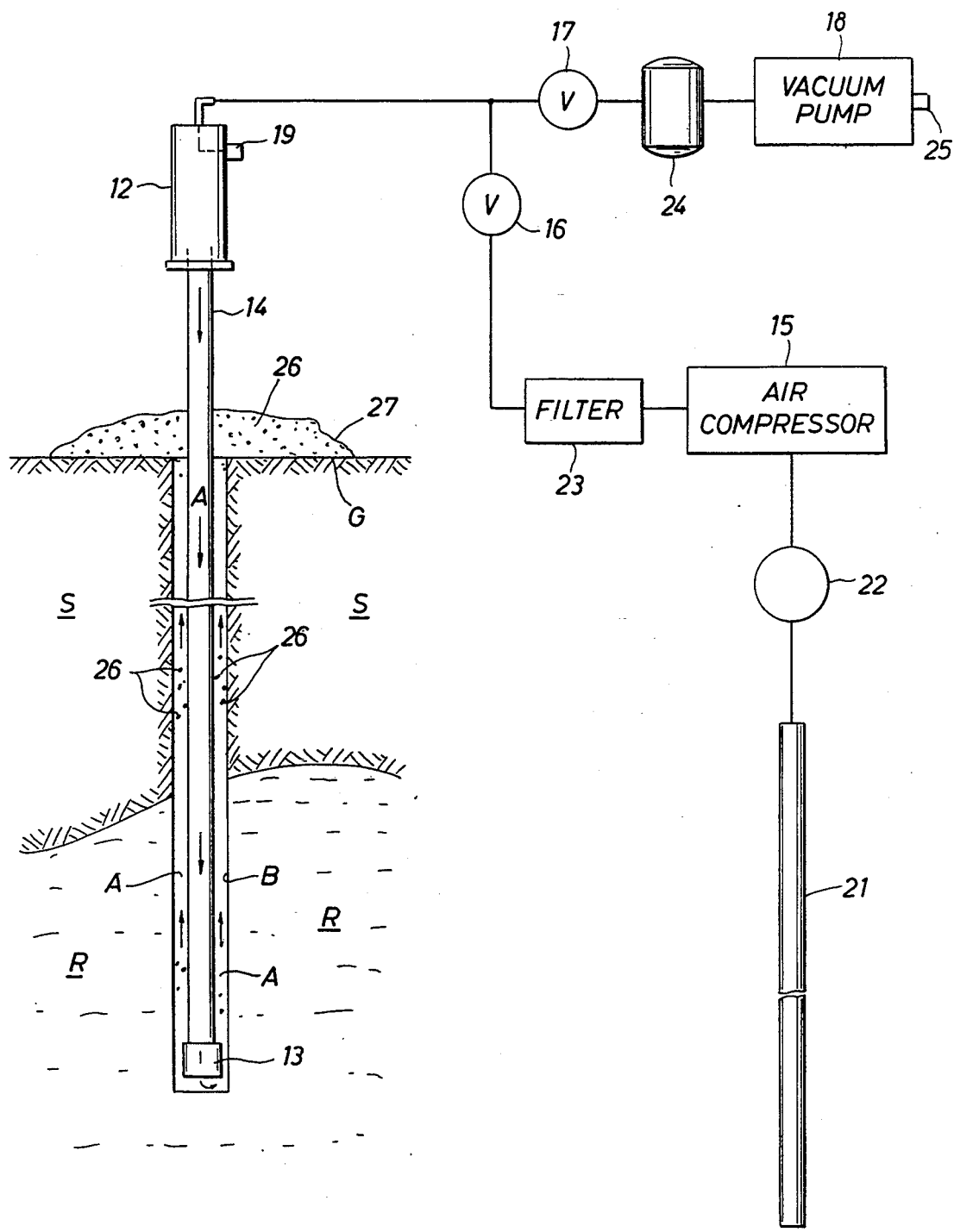
FIG. 2 illustrates the operation of the system.

In general, a drilling apparatus and method is disclosed for sampling and analyzing soil vapors, collecting soil and water samples, completing ground water monitoring wells, and/or installing and testing air sparging/vacuum extraction remediation systems which can be utilized to survey through alluvial soil S and bedrock R, as illustrated in FIG. 2. In operation a portable rotary percussion drilling machine pneumatically drives a drill bit through the soil S, bedrock R, and/or alluvial materials to be prospected for vapor phase, soil, bedrock, and/or ground water contamination. Air A, as the circulation fluid, is injected down the hollow stem of the drill rod 14 and through the perforated drill bit 13. The circulation air A displaces drill cuttings 26 from the boring B which are collected at the surface on plastic sheet 27. Once the drill bit reaches a target depth, the air source for drilling and cleaning out the boring is disconnected and a vacuum pump 18 is connected to the hollow stem of the drill rod. Suitable means for connecting the pump can be devised, given the selection of a particular size and style of pump and a particular size and style of driver. The means may include a valve 17 and a vessel 24 for collecting water samples. The vacuum pump extracts vapors from the soil or bedrock through the hollow drill rod and the perforated drill bit, sometimes referred to in this function as the probe tip. The vapors may then be field screened for vapor concentration, using equipment known in the art, and/or collected for analysis. Both operations may be performed at the exhaust 25 of pump 18. If desired, the probe tip and hollow drill rod may also be used to vacuum water samples from the formation for laboratory analysis.

As the drill bit approaches the target depth, if the bit is in alluvial materials, the air may be turned off, the drill stopped, and the drill physically pushed for the last inch or so. If the target depth lies within bedrock, the above technique is not possible, but also it is not important.

After vapor and/or ground water collection is complete, the vacuum pump is disconnected. At this point the drill rod and bit may be withdrawn from the borehole and the bit replaced by a soil/bedrock sampling tool 20. Given the size and style of drill rod selected and the type of soil sampling tool, specific means can be devised to connect the tool to the drill rod. The rod and tool is then placed back into the borehole and the soil or bedrock sampled by pneumatically driving the tool, which may be a split spoon sampler, into the target horizon. The rod and tool are subsequently withdrawn from the borehole and the soil sample is collected. The rod and rock bit are then placed back into the borehole, the pneumatic driver reconnected, and the process is repeated.

Once the lowest target depth is achieved, usually by 40 or 50 feet, and if contamination is confirmed, airsparging and/or vacuum extraction piping 21 may be installed in the borehole in preparation for remediation. All downhole rods are withdrawn from the boring and the drilling mechanism may be utilized, if or when necessary, to facilitate installing the piping. Subsequent to installation, the air compressor which drives the drilling mechanism is connected to the sparge/vacuum pipe and air is injected into the piping. Air pressure and air flow rate data are monitored at the injection point and at locations of varying distances from the injection point to be used to determine the effective air permeability of the soils/bedrock. This data enables the more efficient design of a remediation system which may use air sparging/vacuum extraction independently or together.

Figure 1:
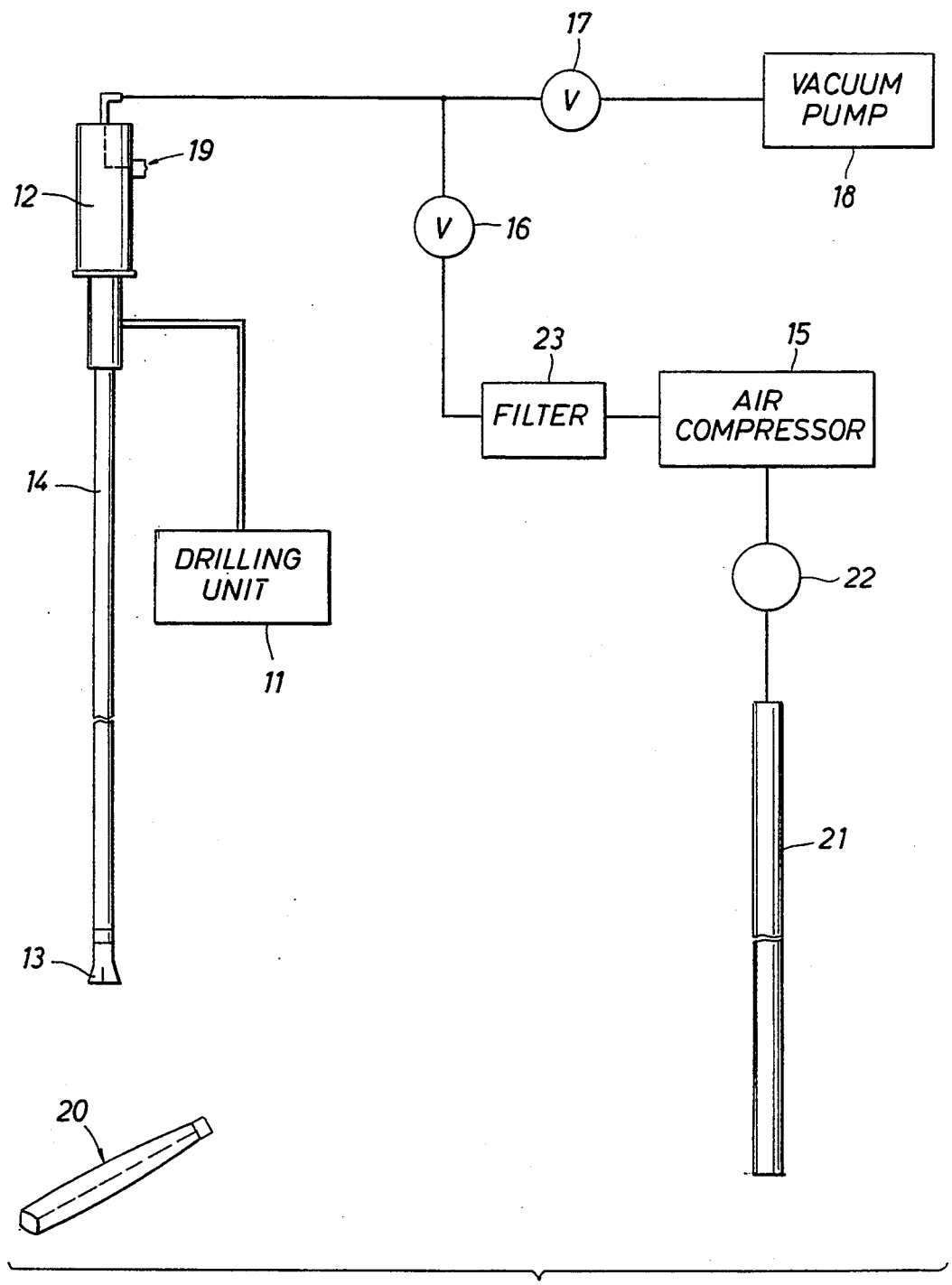
FIG. 1 illustrates the drilling machine and air compressor equipment.

More particularly in reference to the equipment, FIG. 1 shows a pneumatic driver 12, controlled by means of drilling unit 11 and utilizing air compressor 15 to pneumatically drive a perforated rock drill bit 13 into soil, bedrock, and/or alluvial materials to be prospected for vapor phase, soil, bedrock, and/or ground water contamination. The drilling mechanism effects a percussion drilling with some rotation. Air from the compressor 15 is filtered by filter 23 to limit the introduction of contaminants, such as hydrocarbons, into the boring of the system.

The equipment illustrated in FIG. 1 can be loaded on a fifteen foot long flatbed truck. Drilling unit 11 controls driver 12 and compressed air source 15. In one preferred embodiment, pneumatic driver 12 is of a type that is the standard driver for Ingersoll-Rand wagon or air track drills and is similar to an Ingersoll-Rand YD90 Drifter. A suitable driver can be purchased from Ingersoll-Rand and will be approximately two feet long and up to one foot in diameter. Such driver is suitable for penetrating depths shallower than five hundred feet, which covers the region of interest for environmental surveys. A suitable compressed air source would be an Ingersoll-Rand 250 cfm (cubic feet per minute) air compressor or larger. Suitable air filters can be purchased from W.W. Grainger, Inc. Rock bit 13 is a standard rock bit with diameter ranging from 1.75 to 4.0 inches and can be purchased from IMSCO, Inc.

Air from compressor 15 is also injected, through valve 16, down the hollow stem of the drill rod 14 and through perforated rock drill bit 13. The air circulation fluid A displaces drill cuttings 26 from the boring B. These cuttings 26 are carried to the surface and collected on a plastic sheet 27 in the preferred embodiment, as shown in FIG. 2. The hollow drill rod 14 is preferably of one inch to 1.5 inches in diameter and hexagonal in cross-section.

Once the drill bit reaches a target depth, the air compressor source 15 for drilling and cleaning out the boring is disconnected and a vacuum pump 18 is connected through valve 17 to the pneumatic driller 12 and to the hollow stem drill rod 14. Vacuum pump 18 extracts vapors from the soil or bedrock through the perforated rock drill bit, operating as a probe tip, and through the hollow rod. The vapors may be collected and/or metered at the pump exhaust 25. The vapors are field screened for vapor concentration and/or saved for analysis. If desired, the probe tip and hollow stem drill rod can also be used to vacuum water samples from the formation for laboratory analysis. The water samples are collected in vessel 24 located in the line communicating the vacuum pump with the driller. If soil vapor only is collected, vessel 24 is removed from the vacuum line.

The vacuum pump used to extract soil vapor and/or ground water samples in the preferred embodiment is similar to a Dayton No. 4Z336 one-half HP (horsepower) vacuum pump which can be purchased from W.W. Grainger, Inc.

After vapor and/or ground water collection is complete, vacuum pump 18 is disconnected. At this point hollow drill rod 14 and rock bit 13 may be withdrawn from the borehole and the rock bit replaced by soil/bedrock sampling tool 20. The soil/bedrock sampling tool can be a standard 2" o.d. split spoon sampler which can be purchased from Mills Machine Shop. The drill rod is then placed back into the borehole and the soil or bedrock sampled by pneumaticly driving, using driving mechanism 12, soil sampling tool 20 into the target horizon. Drill rod 14 and soil sampling tool 20 are then withdrawn and the soil sample is collected. The drill rod 14 and rock bit 13 are then placed back into the borehole, the pneumatic driver reconnected, and the process is repeated.

Once the lowest target depth is achieved all downhole equipment is withdrawn from the borehole. If contamination is confirmed, air-sparging and/or vacuum extraction piping 21, shown only illustratively in FIGS. 1 and 2, may be installed in the borehole in preparation for commencing remediation.

The typical air sparge/vacuum extraction piping is PVC pipe. To install 2" PVC piping, a 3" borehole is drilled and the pipe then placed down the borehole. If the borehole caves, free fall emplacement of the piping is not possible. In this situation, the piping is installed by using the pneumatic driver to drive the pipe into the wall using a wooden buffer such as a two by four. At this point air compressor 15 may be connected to the installed sparge/vacuum pipe, utilizing some connection device suitable for the size of piping and the compressor hose, and air is injected into the piping. The sparge/vacuum connectors would be designed based on hose size and the outlet provided by the piping used. The air pressure and flow rate may be monitored utilizing air flow meters 22 placed at the injection point and at boring depths located varying distances from the injection point. The air flow meters can be a type similar to 4" magnehelic differential pressure gauges and can be purchased from W.W. Grainger, Inc. This data is then used to determine the effective air permeability of the soils/bedrock for a more efficient design of a remediation system which uses air sparging/vacuum extraction independently or together.

Having described the invention above, various modifications of the techniques, procedures, material and equipment will be apparent to those in the art. It is intended that all such variations within the scope and spirit of the appended claims be embraced thereby.

We claim:

1. Apparatus for environmental surveying for contaminants in alluvial materials and bedrock formations comprising:
    a portable pneumatic rotary percussion drilling machine having pneumatic rotary percussion driver, hollow stem drill rod connected to the driver to transmit rotary percussion motion, a perforated rock drill bit connected to the drill rod and an air compressor connected to the driver such that compressed air is communicated through the hollow stem;
    a vacuum pump; and
    means for connecting the pump with the hollow stem drill rod.

2. The apparatus of claim 1, including means for collecting cuttings from the air circulation fluid.

3. The apparatus of claim 1, including means for collecting fluids pumped up the hollow stem drill rod.

4. The apparatus of claim 3, including means for testing collected fluids for contaminants.

5. The apparatus of claim 1, including a soil and bedrock sampling tool and means for connecting the tool to the drill rod.

6. The apparatus of claim 1, that further includes air-sparging and vacuum extraction piping for installation into a drilled borehole and means for connecting the air compressor to the installed piping.

7. The apparatus of claim 6 that includes meters for monitoring air pressure and air flow rate in the installed piping.

8. The apparatus of claim 1 that includes a means for measuring soil vapor concentration connected to the exhaust of the vacuum pump.

9. The apparatus of claim 1 wherein the drill rod is hexagonal.

10. A method for environmental sampling and monitoring alluvial soil and bedrock comprising:
    pneumatically drilling a borehole with a portable rotary percussion drilling machine having a perforated rock drill bit and hollow stem drill rod;
    circulating air fluid through the stem and borehole, thereby displacing drill cuttings;
    connecting a vacuum pump to the hollow stem drill rod; and
    lifting underground fluid through the bit and up the rod.

11. The method of claim 10 that includes collecting extracted fluids.

12. The method of claim 10 that includes analyzing extracted fluids for contaminants.

13. The method of claim 10 that includes replacing the drill bit with a soil and bedrock sampling tool and pneumatically driving the tool to collect soil samples at a target depth.

14. The method of claim 10 that includes withdrawing the drill rod and drilling machine from the borehole and installing air-sparging and vacuum extraction piping in the borehole.

15. The method of claim 14, wherein the drilling machine includes an air compressor and that further comprises connecting the air compressor to the piping and injecting air into the piping.

16. The method of claim 15 that includes monitoring air pressure and air flow rate of the injected air in the piping.

* * * * *